United States Patent [19]
Tzeng et al.

[11] Patent Number: 5,962,460
[45] Date of Patent: Oct. 5, 1999

[54] ANTINEOPLASTIC α-METHYLENE-γ-BUTYROLACTONES

[75] Inventors: Cherng-Chyi Tzeng; Kuan-Han Lee; Yeh-Long Chen; Bor-Ruey Huang, all of Kaohsiung, Taiwan

[73] Assignee: National Science Council (Taiwan), Taipei, Taiwan

[21] Appl. No.: 08/495,212

[22] Filed: Jun. 27, 1995

[51] Int. Cl.[6] .................... C07D 239/54; C07D 239/553; A61K 31/505

[52] U.S. Cl. .................... 514/274; 514/242; 544/182; 544/313; 544/314; 544/312; 544/311

[58] Field of Search .................... 544/313, 314, 544/311, 312, 182; 514/274, 242

[56] References Cited

PUBLICATIONS

Huang, B. et al. *Chemical Abstract,* No. 121:245284, the abstract of *Gaoxiong Yixue Kexue Zazhi,* vol. 9, pp. 707–711, published in 1993 (Nov. 1994).

Huang, B. et al. *Chemical Abstract,* No. 116:128491, the abstract of *Zhonghua Yaoxue Zazhi,* vol. 43, pp. 447–455, published in 1991 (Mar. 1992).

Winograd, B. *Oxford Textbook of Oncology,* vol. 1, ed. by Peckham, M, et al. (Oxford University Press, Oxford), pp. 486–495 (1995).

Workman, P. et al. *Oxford Textbook of Oncology,* vol. 1, ed. by Peckham, M. et al. (Oxford University Press, Oxford), pp. 495–513 (1995).

Crilley, P.A. et al. *Basic Pharmacology in Medicine,* ed. by DiPalma, J.R. et al. (Medical Surveillance Inc., West Chester), pp. 659–661 (1994).

Cleton, F.J. *Oxford Textbook of Oncology,* vol. 1, ed. by Peckham, M. et al. (Oxford University Press, Oxford), pp. 445–453 (1995).

*Primary Examiner*—John M. Ford
*Attorney, Agent, or Firm*—Chi Ping Chang

[57] ABSTRACT

The present invention provides antineoplastic α-methylene-γ-butyrolactones represented by the general formula [I] wherein $R_1$ is a phenyl group optionally substituted with one or two groups selected from the group consisting of halide, $(C_1-C_4)$alkyl, $(C_1-C_4)$alkoxy, phenyl, nitro and amino; $R_2$ represents hydrogen, halide, $(C_1-C_4)$alkyl or benzyl; X represents N; or wherein $R_1$ is a phenyl group optionally substituted with one or two groups selected from the group consisting of halide, $(C_1-C_4)$alkyl, $(C_1-C_4)$ alkoxy, nitro and amino; $R_2$ represents Cl, F, or benzyl; X represents CH. These α-methylene-γ-butyrolactones may be administered with an inert diluent or with a pharmaceutically acceptable carrier in controlling the growth of a neoplasm in a patient afflicted with a neoplasm disease.

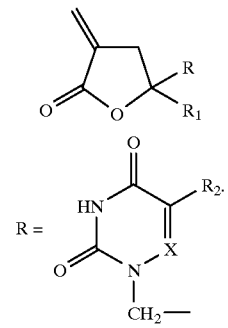

4 Claims, No Drawings

ANTINEOPLASTIC α-METHYLENE-γ-BUTYROLACTONES

TECHNICAL FIELD OF THE INVENTION

The present invention relates to the therapeutical application of α-methylene-γ-butyrolactone derivatives.

BACKGROUND OF THE INVENTION

α-methylene-γ-butyrolactone constitute an important group of natural products which possess wide-ranging biological activities, including antineoplastic, bactericidal, fungicidal, antibiotic and anthelminthic properties (Hoffmann et al., Angew. Chem. Int. Ed. Engl., 1985, 24, 94). The present invention relates to the synthesis and measurement of novel antineoplastic α-methylene-γ-butyrolactones to be used in cancer therapy.

A number of sesquiterpenes bearing α-methylene-γ-butyrolactone functionality such as helenaliry, and elephantopin have exhibited significant antitumor activities(Lee et al., J. Med. Chem., 1972, 15, 609). It was soon characterized that the structural requirement for the cytotoxicity is O=C—C=$CH_2$ moiety which acts as an alkylating agent by a Michael-type reaction with biological cellular nucleophiles or sulphydryl-containing enzymes, leading to the breakage of DNA/RNA or the inhibition of enzyme activities(Kupchan et al., Science, 1970, 168, 376). Other clinically useful alkylating drugs against human malignancy are nitrogen mustards: uracil mustard, chloroambucil and cyclophosphamide. Their utilization is, however, limited by the poor selectivity and the serious side effects such as bone marrow toxicity. The individual drugs also produce distinctive toxic effects on the intestine, kidneys, heart and other organs. Therefore, efforts have been made wordwide to discover more active and less toxic antineoplastic agents. Certain α-methylene-γ-butyrolactones had been prepared and screened (Lee et al., J. Med. Chem., 1977, 20,911; Heindel et al., J. Pharm. Sci., 1981, 70, 84; Sanyal et al., J. Med. Chem., 1986, 29, 595) . Recently, we described the synthesis and cytotoxicity of certain uracil α-methylene-γ-butyrolactones and uncovered that an aryl substituent at 5-position of the α-methylene-γ-butyrolactone ring enhanced the antitumor potency (Chin. Pharm. J. 1991, 43, 447; Kaohsiung J. Med. Sci., 1993, 9, 707). The present invention describes the preparation of certain novel α-methylene-γ-butyrolactones as antineoplastic agents. All compounds were evaluated in vitro against a total of 56 human tumor cell lines derived from nine cancer types.

DETAILED DESCRIPTION OF THE INVENTION

The present inventors have discovered four classes of novel compounds with excellent antineoplastic activity. As a result of intensive studies, it has been found that compounds represented by the formula [I–IV] have shown not only potent but also selective in inhibiting cancer cells.

The present invention provides antineoplastic α-methylene-γ-butyrolactones represented by the general formula [I–IV]:

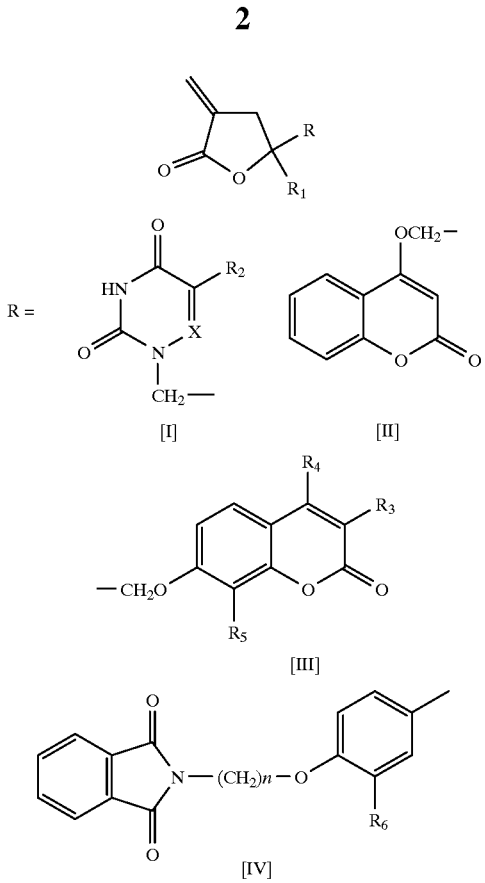

For the formula [I], $R_1$ is a phenyl group optionally substituted with one or two groups selected from the group consisting of halide, ($C_1$–$C_4$) alkyl,($C_1$–$C_4$)alkoxy, phenyl, nitro and amino; $R_2$ represents hydrogen, halide, ($C_1$–$C_4$) alkyl or benzyl; X represents CH or N.

For the formula [II], $R_1$ is a methyl or a phenyl group optionally substituted with one or two groups selected from the group consisting of halide, ($C_1$–$C_4$) alkyl, ($C_1$–$C_4$) alkoxy, phenyl, nitro and amino.

For the formula [III], $R_1$ is a methyl or a phenyl group optionally substituted with one or two groups selected from the group consisting of halide, ($C_1$–$C_4$) alkyl, ($C_1$–$C_4$) alkoxy, phenyl, nitro and amino; $R_3$ represents hydrogen, halide, ($C_1$–$C_4$) alkyl, phenyl, nitro or amino; $R_4$ represents hydrogen, halide, ($C_1$–$C_4$) alkyl, phenyl, nitro or amino; $R_5$ represents hydrogen, ($C_1$–$C_4$)alkyl, (3-methylene-2-oxo-5-furanyl)methoxy, hydroxyl, or ($C_1$–$C_7$)alkoxy.

For the formula [IV], $R_1$ is a hydrogen; R6 represents hydrogen, halide, ($C_1$–$C_4$)alkyl or ($C_1$–$C_4$)alkoxy; n represents ($C_3$–$C_8$)alkyl.

The present invention also provides a cost-efficient method for the preparation of formula [I–IV].

Formula [I–IV] may be administered with an inert diluent or with a pharmaceutically acceptable carrier in controlling the growth of a neoplasm in a patient afflicted with a neoplasm disease.

This invention included the preparation and the antitumor evaluation of novel α-methylene-γ-butyrolactones which have been proved to be active against the growth of leukemia (CCRF-CEM, HL-60, MOLT-4, etc.), colon(COLO 205, HCT-l16, HT-29, etc.) cancer cell lines, etc. These active compounds, as free type or their pharmaceutically acceptable salts, may be administered parenterally or orally in a suitable pharmaceutical form. They also may be administered along or in conjunction with other antitumor agents, in combination with any pharmaceutically acceptable carrier.

As used herein, the pharmaceutically acceptable salts include salts with inorganic acids, such as hydrochloride, hydrobromide, sulfate and phosphate; those organic acids, such as acetate, maleate, tartarate, methanesulfonate; and those with amino acids, such as arginine, aspartic acid and glutamic acid. Suitable pharmaceutical forms include sterile aqueous solutions or dispersions, sterile powders, tablets, troches, pills, capsules, and the like. In addition, the active compounds may be incorporated into sustained-release preparations and formulations. The pharmaceutically acceptable carrier includes any and all solvents, disintegrating agents, binders, excipients, lubricants, absorption delaying agents and the like. Although the compound of the present invention may also be present as a hydrate or as a stereoisomer, it is a matter of course that these hydrates and stereoisomers are also included in the scope of the present invention.

The new compounds can be prepared according to the following reaction schemes and protocols.

PART A

Preparation of 5-Aryl-3-methylene-2-oxo-5-(pyrimidin-1-ylmethyl)-tetrahydrofuran

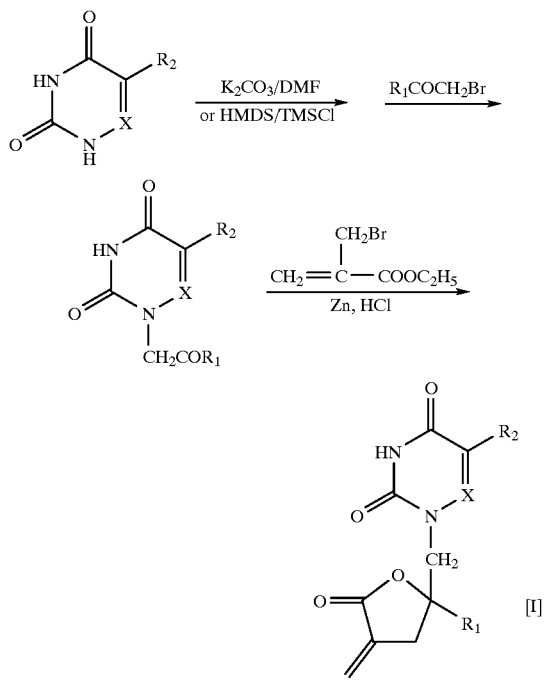

(Scheme 1)

Uracil or its derivative was either silylated with hexamethyldisilazane(HMDS) and a catalytical amount of chlorotrimethylsilane(TMSCl)followed by the alkylation or was directly alkylated with a commercially available aryl bromomethyl ketone(2-bromoacetophenone, $R_1=C_6H_5$; 2-bromo-4'-fluoroacetophenone, $R_1=C_6H_4F$; 2-bromo-4'-chloroacetophenone, $R_1=C_6H_4Cl$; 2-bromo-4'-bromoacetophenone, $R_1=C_6H_4Br$; 2-bromo-4'-iodoacetophenone, $R_1=C_6H_4I$; 2-bromo-4'-methylacetophenone, $R_1=C_6H_4CH_3$; 2-bromo-4'-nitroacetophenone, $R_1=C_6H_4NO_2$; 2-bromo-4'-methoxyacetophenone, $R_1=C_6H_4OCH_3$; 2-bromo-4'-phenylacetophenone, $R_1=C_6H_4C_6H_5$) in the presence of potassium carbonate ($K_2CO_3$) and N,N-dimethylformamide (DMF) to afford the 1-ketonyl pyrimidines. Reformatsky-type reaction between ethyl 2-(bromomethyl)acrylate and the respective 1-ketonyl pyrimidines under nitrogen atmosphere produced the desired 5-aryl-3-methylene-2-oxo-5-(pyrimidin-1-ylmethyl)-tetrahydrofuran in good yield.

EXAMPLE 1

5-(5-Bromouracil-1-ylmethyl)-3-methylene-2-oxo-5-p-phenyl-phenyl)-tetrahydrofuran (1)

Bromouracil(1.91 g, 10 mmol), potassium carbonate (1.38 g, 10 mmol) and dry N,N-dimethylformamide (DMF) (40 ml) were stirred at room temperature under nitrogen atmosphere for 30 min. To this solution, 2-bromo-4'-phenylacetophenone(2.75 g, 10 mmol) in dry DMF(10 ml) was added at one portion. The resulting solution was stirred at room temperature for 48 h (monitored by TLC) and then poured into ice water (50 ml). The resulting pale yellow solid was filtered, washed with cold water(10 ml), and crystallized from methanol to afford 1-p-phenylphenacyluracil(1a) (1.94 g, 63%).

To the mixture of 1a(307 mg, 1 mmol), activated zinc powder(Aldrich® 32,493-0,-100 mesh, 99.998%) (85 mg, 1.3 mmol), and p-hydroquinone(2 mg) in dry tetrahydrofuran(THF) (20 ml) was added dropwise a solution of ethyl 2-(bromomethyl)acrylate(260 mg, 1.3 mmol) in dry THF(5 ml). The reaction mixture was refluxed under nitrogen atmosphere for 4 h. After cooling it was poured into an ice-cold 5% HCl solution (100 ml) and extracted with dichloromethane(50 ml×3). The dichloromethane extracts were combined and washed with saline, dried over anhydrous magnesium sulfate, and then evaporated to give a white solid which was crystallized from ethyl acetate. The white crystal was died in vaccuo at 80° C. over $P_2O_5$ afforded the title compound in a quantitative yield.

mp 238–241° C.; yield 69%;

UV λ max: 257.2(0.1 N HCl/$CH_3OH$), 257.0($CH_3OH$), 254.2(0.1 N NaOH/$CH_3OH$);

$^1$H-NMR(DMSO-$d_6$): δ 3.40 (m, 2H, 4-$CH_2$), 4.26 & 4.31 (2d, 2H, $NCH_2$), 5.73 (t, 1H, vinylic H), 6.04 (t, 1H, vinylic H), 7.57 (m, 9H, Ar—H), 7.89 (s, 1H, 6-CH), 11.79 (brs, 1H, NH);

Anal. for $C_{22}H_{17}N_2O_4Br$: Calcd.: C, 58.29; H, 3.78; N, 6.18. Found : C, 58.43; H, 3.50; N, 6.01.

EXAMPLE 2

3-Methylene-2-oxo-5-(p-phenylphenyl)-5-(thymin-1-ylmethyl)-tetrahydrofuran (2)

The title compound was synthesized from thymine and 2-bromo-4'-phenylacetophenone according to the procedures described above for the preparation of 1:

mp 217–219° C.; yield 93%;

$^1$H-NMR(CDCl$_3$): δ 1.71 (d, 3H, $CH_3$), 3.40 (m, 2H, 4-$CH_2$), 4.10 & 4.34 (d, 2H, $NCH_2$), 5.70 (t, 1H, vinylic H), 6.01 (t, 1H, vinylic H), 7.29 (d, 1H, 6-CH), 7.57 (m, 9H, Ar—H), 11.29 (brs, 1H, NH);

Anal. for $C_{23}H_{20}N_2O_4$: Calcd.: C, 71.12; H, 5.19; N, 7.21. Found : C, 71.11; H, 5.28; N, 7.26.

EXAMPLE 3

5-(p-Chlorophenyl)-3-methylene-2-oxo-5-(thymin-1-ylmethyl)-tetrahydrofuran (3)

Compound 3 was prepared from thymine and 2-bromo-4'-chloroacetophenone according to the procedure given for 1:

mp 188–189° C.; yield 78%;

UV λ max: 269.0(0.I N HCl/CH$_3$OH), 269.0 (CH$_3$OH), 272.0(0.I N NaOH/CH$_3$OH).

$^1$H-NMR(CDCl$_3$): δ 1.90 (d, 3H, CH$_3$), 3.32 (m, 2H, 4-CH$_2$), 3.78 & 4.46 (d, 2H, NCH$_2$), 5.63 (t, 1H, vinylic H), 6.18 ( t, 1H, vinylic H), 7.08 (d, 1H, 6-CH), 7.35 (m, 4H, Ar—H), 8.95 (br s, 1H, NH);

Anal. for C$_{17}$H$_{15}$N$_2$O$_4$Cl: Calcd.: C, 58.88; H, 4.36; N, 8.08. Found : C, 58.73; H, 4.57; N, 8.39.

PART B

Preparation of 4-[(2,3,4,5-tetrahydro-3-methylene-2-oxo-5-furanyl)-methoxy]-2H-1-benzopyran-2-ones [II] and 7-[(2,3,4,5-tetrahydro-3-methylene-2-oxo-5-furanyl) methoxy]-2H-1-benzopyran-2-ones [III]

(Scheme 2)

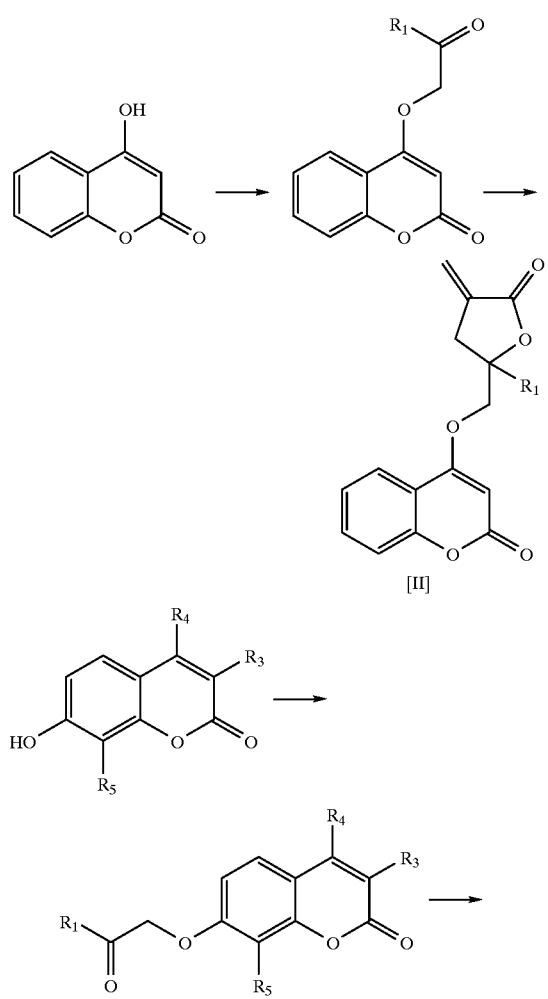

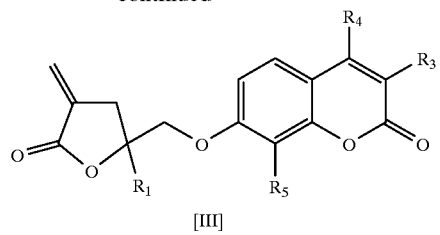

[III]

Each of the commercially available 4-hydroxycoumarin, 7-hydroxycoumarin(R$_3$=R$_4$=R$_5$=H), 7-hydroxy-4-methylcoumarin(R$_4$=CH$_3$), 3-chloro-7-hydroxy-4-methylcoumarin(R$_3$=Cl, R$_4$=CH$_3$), and 7-hydroxy-3,4,8-trimethylcoumarin (R$_3$=R$_4$=R$_5$=CH$_3$) was treated with potassium carbonate and a haloketone (chloroacetone, R$_1$=CH$_3$; 2-bromoacetophenone, R$_1$=C$_6$H$_5$; 2-bromo-4'-fluoroacetophenone, R$_1$=C$_6$H$_4$F; 2-bromo-4'-chloroacetophenone, R$_1$=C$_6$H$_4$Cl; 2-bromo-4'-bromoacetophenone, R$_1$=C$_6$H$_4$Br; 2-bromo-4'-iodoacetophenone, R$_1$=C$_6$H$_4$I; 2-bromo-4'-methylacetophenone, R$_1$=C$_6$H$_4$CH$_3$; 2-bromo-4'-nitroacetophenone, R$_1$=C$_6$H$_4$NO$_2$; 2-bromo-4'-methoxyacetophenone, R$_1$=C$_6$H$_4$OCH$_3$; 2-bromo-4'-phenylacetophenone, R$_1$=C$_6$H$_4$C$_6$H$_5$) in acetone to provide (2-oxo-2-phenyl ethoxy)-2H-1-benzopyran-2-one which was reacted with ethyl 2-(bromomethyl)acrylate in tetrahydrofuran(THF) (Reformatsky reaction) to produce 4-[(2,3,4,5-tetrahydro-3-methylene-2-oxo-5-furanyl) methoxy]-2H-1-benzopyran-2-ones and 7-[(2,3,4,5-tetrahydro-3-methylene-2-oxo-5-furanyl)-methoxy]-2H-1-benzopyran-2-ones as shown in Scheme 2.

EXAMPLE 4

4-[(2,3,4,5-Tetrahydro-3-methylene-2-oxo-5-phenyl-5-furanyl)methoxy]-2H-1-benzopyran-2-one (4)

To a solution of 4-hydroxycoumarin(1.62 g, 10 mmol) in acetone(60 ml) were added 2-bromoacetophenone(1.99 g, 10 mmol) and potassium carbonate (5.53 g, 40 mmol) . The mixture was refluxed for 3 h. (monitored by TLC). Evaporation of the solvent gave a residue which was poured into ice water(50 ml). The resulting solid was collected and crystallized from ethyl acetate to afford 4-(2-oxo-2-phenylethoxy)-2H-1-benzopyran-2-one(4a) (1.76 g, 62.9%) as a needle crystal. mp: 183–184° C.

To a solution of 4a(0.84 g, 3 mmol) in dry tetrahydrofuran (60 ml) were added activated zinc powder (0.255 g, 3.9 mmol), hydroquinone(6 mg), and ethyl 2-(bromomethyl)acrylate(0.78 g, 4 mmol). The mixture was reflued under nitrogen atmosphere for 8 h. (monitored by TLC). After cooling it was poured into an ice-cold 5% HCl solution (300 ml) and extracted with CH$_2$Cl$_2$(75 ml×3). The dichloromethane extracts were combined and washed with saline, dried over Na$_2$SO$_4$, and then evaporated to give a residual solid which was crystallized from ethyl acetate to afford the title compound(0.90 g, 86.4%).

mp: 212–214° C.;

IR(KBr) V max: 1766, 1717, 1620;

UV(CHCl$_3$) λ max(log ε): 306 (3.89), 277 (4.10), 266 (4.14);

$^1$H-NMR (CDCl$_3$): δ 3.33–3.66 (m, 2H, 4-CH$_2$), 4.26–4.32 (m, 2H, OCH$_2$), 5.60 (s, 1H, 3-H), 5.79 (t, 1H, vinylic H), 6.42 (t, 1H, vinylic H), 7.20–7.61 (m, 9H, 5,6,7,8-H, and aromatic H);

Anal. for $C_{21}H_{16}O_5$ 0.25 $H_2O$: Calcd.: C, 71.48, H, 4.71. Found : C, 71.37, H, 4.67.

EXAMPLE 5

7-[(2,3,4,5-Tetrahydro-5-methyl-3-methylene-2-oxo-5-furanyl)methoxy]-2H-1-benzopyran-2-one (5)

Compound 5 was prepared from 7-hydroxycoumarin and chloroacetone according to the procedure given for 4: yield: 79.7%;

mp: 123–124° C.;

IR(KBr) V max: 1755, 1727, 1626;

UV(CHCl$_3$) λ max(log ε): 312 (4,18), 243 (3.58);

$^1$H-NMR(CDCl$_3$): δ 1.58 (s, 3H, 5-CH$_3$), 2.79–3.18 (m, 2H, 4-CH$_2$), 3.99–4.09 (m, 2H, OCH$_2$), 5.69 (t, 1H, vinylic H), 6.26 (d, 1H, 3-H), 6.29 (t, 1H, vinylic H), 6.76-7.65 (m, 4H, Ar—H);

Anal. for $C_{16}H_{14}O_5$: Calcd.: C, 67.13; H, 4.93. Found : C, 66.95; H, 5.10.

EXAMPLE 6

7-[(2,3,4,5-Tetrahydro-3-methylene-2-oxo-5-phenyl-5-furanyl)methoxy]-2H-1-benzopyran-2-one (6)

Compound 6 was prepared from 7-hydroxycoumarin and 2-bromoacetophenone according to the procedure given for 4: yield: 77.8%;

mp: 105–106° C.;

IR(KBr) V max: 1758, 1719, 1616;

UV(CHCl$_3$) λ max(log ε): 321 (4.22), 243 (3.62);

$^1$H-NMR(CDCl$_3$): δ 3.24–3.66 (m, 2H, 4-CH$_2$), 4.17–4.24 (m, 2H, OCH$_2$), 5.71 (t, 1H, vinylic H), 6.24 (d, 1H, 3-H), 6.31 (t, 1H, vinylic H), 6.72 (d, 1H, B—H), 6.78 (dd, 1H, 6-H), 7.35 (d, 1H, 5-H), 7.40–7.52 (m, 5H, Ar—H), 7.62 (d, 1H, 4-H);

Anal. for $C_{21}H_{16}O_5$ Calcd.: C, 72.41, H, 4.63. Found : C, 72.30; H, 4.67.

EXAMPLE 7

3-Chloro-7-[(2,3,4,5-tetrahydro-3-methylene-2-oxo-5-phenyl-5-furanyl) methoxy]-4-methyl-2H-1-benzopyran-2-one (7)

Compound 7 was prepared from 3-chloro-7-hydroxy-4-methylcoumarin and 2-bromoacetophenone according to the procedure given for 4, yield: 71%;

mp: 149–150° C.;

IR(KBr) V max: 1762, 1724, 1618;

UV((CHCl$_3$) λ max(log ε): 328 (4.25), 244 (3.69);

$^1$H-NMR(CDCl$_3$): δ 2.52 (s, 3H, CH$_3$), 3.24–3.68 (m, 2H, 4-CH$_2$), 4.18–4.25 (m, 2H, OCH$_2$), 5.71 (t, 1H, vinylic H), 6.31 (t, 1H, vinylic H), 6.73 (d, 1H, 8-H), 6.84 (dd, 1H, 6-H), 7.38–7.52 (m, 6H, 5-H and Ar—H);

Anal. for $C_{22}H_{17}ClO_5$: Calcd.: C, 66.59, H, 4.32. Found: C, 66.23; H, 4.41.

PART C

Preparation of 3-Methylene-2-oxo-5-(p-N-phthalimidopropoxyphenyl)-tetrahydrofuran (Scheme 3)

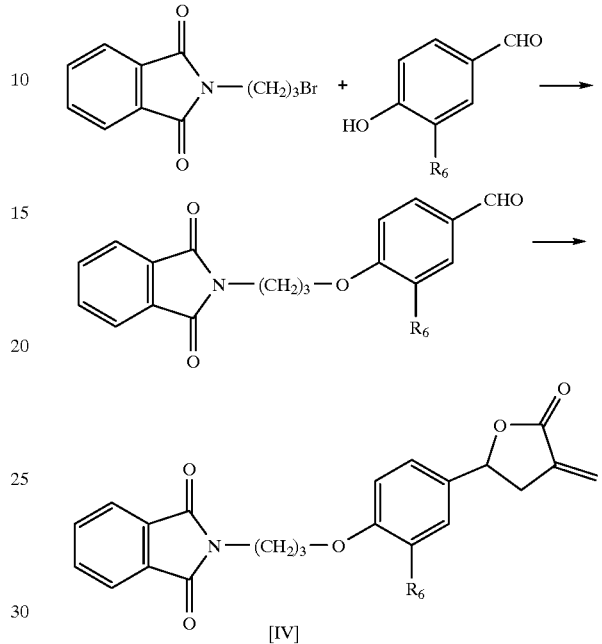

4-Hydroxybenzldehyde (4-hydroxy-3-methoxybenzaldehyde, R$_6$=OCH$_3$) was treated with sodium ethoxide and then alkylated with N-(3-bromopropyl) phthalimide to give p-N-phthalimidopropoxybenzaldehyde which was reacted with ethyl 2-(bromomethyl)acrylate in THF to produce 3-methylene-2-oxo-5-(p-N-phthalimidopropoxyphenyl-tetrahydrofuran.

EXAMPLE 8

3-Methylene-2-oxo-5-(p-N-phthalimidopropoxyphenyl)-tetrahydrofuran (8)

To a solution of 4-hydroxybenzaldehyde(3.18 g, 25 mmol) in ethanol (20 ml) were added sodiun ethoxide (0.58 g sodium in 30ml ethanol) and N-(3-bromopropyl) phthalimide(6.70 g, 25 mmol). The mixture was refluxed for 5 h. (monitored by TLC). The solvent was evaporated to give a residue which was disolved in CHCl$_3$(150 ml), washed with 5% aqueous NaOH (80 ml) and water(80 ml). Evaporation of the solvent provided a residual solid which was crystallized from ethyl acetate to afford p-N-phthalimidopropoxybenz aldehyde (8a) (4.57 g, 59 %) as a needle crystal.

To a solution of 8a(0.93 g, 3 mmol) in dry tetrahydrofuran (60 ml) were added activated zinc powder(0.255 g, 3.9 mmol), hydroquinone (6 mg), and ethyl 2-(bromomethyl) acrylate (0.78 g, 4 mmol). The mixture was reflued under nitrogen atmosphere for 30 h.(monitored by TLC). After cooling it was poured into an ice-cold 5% HCl solution(300 ml) and extracted with CHCl$_3$ (150 ml×2). The extracts were combined and washed with saline, dried over Na$_2$SO$_4$, and then evaporated to give a residual solid which was crystallized from methanol to afford the title compound (0.97 g, 85%).

$^1$H-NMR(CDCl$_3$): δ 2.19 (m, 2H, CH$_2$) 2.89–3.34 (m, 2H, 4-CH$_2$), 3.91 (t, 2H, NCH$_2$), 4.03 (t, 2H, OCH$_2$), 5.45 (t, 1H, 5-H), 5.68 (t, 1H, vinylic H), 6.30 (t, 1H, vinylic H), 6.80 & 7.20 (m, 4H, phenyl), 7.70–7.86 (m, 4H, Ar—H);

Anal. for C$_{22}$H$_{19}$NO$_5$: Calcd.: C, 70.02, H, 5.07, N, 3.71. Found : C, 69.97, H, 5.07, N, 3.53.

In vitro antitumor assay

All compounds were evaluated in vitro against 55 human tumor cell lines derived from nine cancer cell types (leukemia, non-small cell lung cancer, colon cancer, CNS cancer, melanoma, ovarian cancer, renal cancer, prostate cancer and breast cancer). For each compound, dose-response curves for each cell line were measured with five different drug oncentrations, and the concentration causing 50% cell growth inhibition(GI$_{50}$), total cell growth inhibition(TGI, 0% growth) and 50% cell death(LC$_{50}$, −50% growth) compared with the control was calculated. The GI$_{50}$ values of tested compounds are given in Table I. All of them proved to be active against the growth of leukemia(CCRF-CEM, HL-60, MOLT-4, etc.), colon (COLO 205, HCT-116, HT-29, etc.) cancer cell lines, etc.

The log$_{10}$GI$_{50}$, log$_{10}$TGI and log$_{10}$LC50 are expressed in the form of mean graphs, however, only the mean graph midpoint values of log$_{10}$GI$_{50}$, log$_{10}$TGI and log$_{10}$LC50 are listed in Table 2.

We claim:

1. A compound represented by the formula:

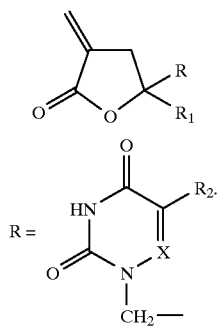

Formula [I], wherein R$_1$ is a phenyl group optionally substituted with one or two groups selected from the group consisting of halide, (C$_1$–C$_4$)alkyl, (C$_1$–C$_4$) alkoxy, nitro and amino; R$_2$ represented Cl, F or benzyl; X represents CH.

2. A pharmaceutical composition for the treatment of leukemia cancer diseases comprises any compound of claim 1 or their salts in combination with any pharmaceutically acceptable carrier.

3. A method of treating leukemia cancerous cell growth in an animal, comprising administrating any compounds of claim 1 or their pharmaceutically acceptable salts in an amount effective to inhibit DNA or RNA replication in tumor cells.

4. A synthetic processes for preparing compounds of claim 1, comprising: silylating uracil or its derivative of formula [V] with hexamethyldisilazane (HMDS) and a catalytical amount of chlorotrimethylsilane (TMSCl) followed by alkylation or, in the alternative, alkylating said uracil or its derivative directly with aryl bromomethyl ketone R1COCH2Br in the presence of potassium carbonate (K2CO3) and DMF (N,N-dimethyl-formamide) to afford the 1-ketonyl pyrimidines of formula [VI]; performing Reformatsky-type reaction between ethyl-2-(bromomethyl) acrylate and the respective 1-ketonyl pyrimidines under nitrogen atmosphere to produce the desired 5-aryl-3-methylene-2-oxo-5-(pyrimidin-1-ylmethyl)-tetrahydrofuran of formula [VII], wherein R$_1$ is a phenyl group optionally substituted with one or two groups selected from the group consisting of halide, (C$_1$–C$_4$) alkyl, (C$_1$–C$_4$) alkoxy, nitro and amino; R$_2$ represented Cl, F or benzyl; X represents CH.

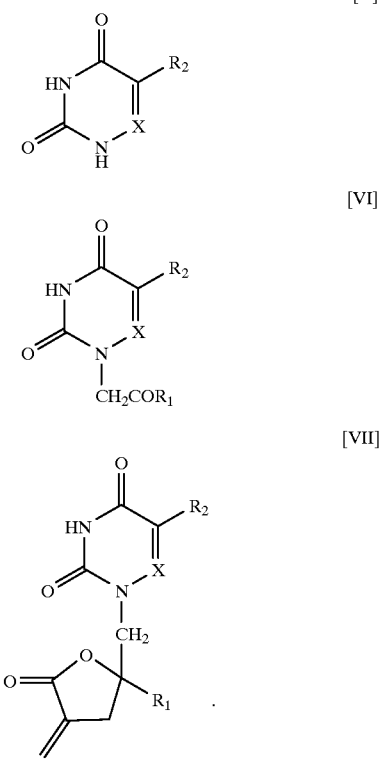

* * * * *